(12) United States Patent
Cirillo (10) Patent No.: US 11,191,905 B2
(45) Date of Patent: Dec. 7, 2021

(54) MONITORING DEVICE (71) Applicant: SHL MEDICAL AG, Zug (CH)

(72) Inventor: William Cirillo, Dublin (IE)

(73) Assignee: SHL MEDICAL AG, Zug (CH)

( * ) Notice: Subject to any disclaimer, the term of this patent is extended or adjusted under 35 U.S.C. 154(b) by 303 days.

(21) Appl. No.: 16/337,687

(22) PCT Filed: Oct. 6, 2017

(86) PCT No.: PCT/EP2017/075505
§ 371 (c)(1),
(2) Date: Mar. 28, 2019

(87) PCT Pub. No.: WO2018/069183
PCT Pub. Date: Apr. 19, 2018

(65) Prior Publication Data
US 2020/0030546 A1    Jan. 30, 2020

(30) Foreign Application Priority Data
Oct. 14, 2016  (EP) .................................. 16193932

(51) Int. Cl.
A61M 5/315    (2006.01)
A61M 5/31     (2006.01)

(52) U.S. Cl.
CPC .... *A61M 5/31568* (2013.01); *A61M 5/31585* (2013.01); *A61M 2005/3126* (2013.01);
(Continued)

(58) Field of Classification Search
CPC .......... A61M 5/31568; A61M 5/31585; A61M 5/20; A61M 5/3155; A61M 2005/3126;
(Continued)

(56) References Cited

U.S. PATENT DOCUMENTS

2005/0096587 A1    5/2005 Santini et al.
2010/0286612 A1*  11/2010 Cirillo ............... A61M 5/31525
                                                            604/111
(Continued)

FOREIGN PATENT DOCUMENTS

CN    1799071 A      7/2006
CN    102427840 A    4/2012
(Continued)

OTHER PUBLICATIONS

"Definition of Interruption." Merriam-Webster Dictionary, <https://www.merriam-webster.com/dictionary/interruption>. Jun. 30, 2021. (Year: 2021).*

(Continued)

*Primary Examiner* — Nathan R Price
*Assistant Examiner* — Tasnim Mehjabin Ahmed
(74) *Attorney, Agent, or Firm* — McDonnell Boehnen Hulbert & Berghoff LLP (57) ABSTRACT

The present disclosure relates to a monitoring device arranged to be operably connected to a medicament delivery device, said medicament delivery device has a manually operated movable dose activating element, said monitoring device having an electronic circuit, said electronic circuit having a light emitting element and a light sensor, wherein said light emitting element and said light sensor are positioned in relation to said dose activating element so as to detect a manual operation of said dose activating element from an initial position.

15 Claims, 6 Drawing Sheets

(52) U.S. Cl.
CPC .......... *A61M 2205/13* (2013.01); *A61M 2205/3306* (2013.01); *A61M 2205/3368* (2013.01); *A61M 2205/3584* (2013.01); *A61M 2205/581* (2013.01); *A61M 2205/582* (2013.01); *A61M 2205/583* (2013.01)

(58) Field of Classification Search
CPC ...... A61M 2205/13; A61M 2205/3306; A61M 2205/3368; A61M 2205/3584; A61M 2205/581; A61M 2205/582; A61M 2205/583; A61M 2205/3561; A61M 2205/587; A61M 2205/3576
See application file for complete search history.

(56) References Cited

U.S. PATENT DOCUMENTS

| | | | |
|---|---|---|---|
| 2012/0053527 | A1 | 3/2012 | Cirillo et al. |
| 2015/0290396 | A1* | 10/2015 | Nagar ................ A61M 5/3202 340/540 |
| 2016/0067409 | A1* | 3/2016 | Blei ........................ A61M 5/31 604/207 |
| 2017/0138769 | A1* | 5/2017 | Jones ................ A61M 5/31525 |

FOREIGN PATENT DOCUMENTS

| | | |
|---|---|---|
| CN | 104203309 A | 12/2014 |
| CN | 105120930 A | 12/2015 |
| WO | 2010/128493 A2 | 11/2010 |
| WO | 2014/173771 A1 | 10/2014 |
| WO | 2015/136513 A1 | 9/2015 |

OTHER PUBLICATIONS

International Search Report and Written Opinion for Int. App. No. PCT/EP2017/075505, dated Jan. 9, 2018.

* cited by examiner

MONITORING DEVICE

CROSS REFERENCE TO RELATED APPLICATIONS

The present application is a U.S. National Phase Application pursuant to 35 U.S.C. § 371 of International Application No. PCT/EP2017/075505 filed Oct. 6, 2017, which claims priority to European Patent Application No. 16193932.7 filed Oct. 14, 2016. The entire disclosure contents of these applications are herewith incorporated by reference into the present application.

TECHNICAL AREA

The present disclosure relates to a monitoring device or unit and in particular a monitoring unit for a medicament delivery device that is capable of obtaining information regarding the use of the medicament delivery device.

BACKGROUND

There are many injectors on the market that are developed for personal use, wherein the patient is self-medicating. One very common type of drug for self-medication is insulin where the patient often uses a pen-type medicament delivery device that often is arranged with a dose activating element, which usually is a knob at the distal end of the medicament delivery device. When setting a dose to be delivered the knob is either turned or pulled in the distal direction. The set dose is often displayed so that the user knows which dose to set. During a subsequent dose delivery or injection, the knob is moved back to its initial position.

Many medicaments such as e.g. insulin have to be taken on a regular and prescribed basis based on an administration schedule, and if not adhered to, may lead to severe consequences for the patient. Because of these demands on the user, several devices have been developed that facilitates the information to the user when to administer a subsequent dose. The document WO 2010/128493 discloses a supervisor device for a medicament delivery device. The supervisor device comprises a monitoring unit that can be attached to a medicament delivery device with the help of a sleeve that is designed to fit onto a certain medicament delivery device. The sleeve could either be integrated with the monitoring unit or be a separate component that is attachable to the monitoring unit.

The monitoring unit is arranged with electronic circuits capable of collecting different data and performing a number of functions with the collected data. Examples of data are dosage and time of each injection of medicament. The monitoring unit may then provide messages to a user via a display, which messages are based on the collected and processed data. The monitoring unit is further arranged with communication elements so as to transmit and receive data to and from external devices such as smart devices and personal computers.

In order to activate the monitoring unit and in order to monitor the users behaviour with the medicament delivery device, a sensor in the form of a micro switch is arranged such on the monitoring unit that when the monitoring unit is attached to a medicament delivery device, the micro switch is in contact with a side surface of a dose activating element of the medicament delivery device. When a user is setting a dose for administering a dose of medicament, the dose setting element is moved in the distal direction whereby the micro switch is activated. The activation of the micro switch causes the electronics of the monitoring unit to be energized. This will cause a timer of the electronics units to be reset, which is displayed on a display. When the proper dose volume has been set, the medicament delivery device is placed against an injection site and the dose activating element is moved back to the initial position manually by a user, causing an injection of medicament. When the dose activating element is back in its initial position, the micro switch is closed, which triggers the electronics circuit to start a timer, which also is displayed on the display.

Even if the monitoring unit according to WO 2010/128493 works well, there might be instances where a mechanical activation of the monitoring unit is not optimal.

SUMMARY

The aim of the present disclosure is to remedy the drawbacks of the state of the art technology. This aim is obtained by a monitoring device comprising the features of the independent patent claim. Preferable embodiments form the subject of the dependent patent claims.

According to the disclosure, it comprises a monitoring device arranged to be operably connected to a medicament delivery device wherein the medicament delivery device comprises a manually operated movable dose activation element. The monitoring device may preferably comprise an electronics circuit, wherein the electronics circuit may comprise a light emitting element and a light sensor. Further the light emitting element and the light sensor may be positioned in relation to the dose activation element so as to detect a manual operation of said dose activation element from an initial position. The advantage with this solution is that there is no physical contact between the monitoring device and the dose activation element, and thus no components can be worn or damaged due to contact.

Preferably the dose activation element is arranged for setting a dose of medicament and for delivering said set dose. This is a very common solution for a so called pen injector. In this regard, the light emitting element and the light sensor may be positioned in relation to the dose activation element so that a light beam between the light emitting element and the light sensor is interrupted when the dose activation element is in its initial position, is uninterrupted when the dose activating element is moved from its initial position, and is again interrupted when the dose activating element is returned to its initial position after delivery of a dose. Thus, the interruption of the light beam creates occurrences that may be used by the monitoring device, such that the electronics circuit may be arranged to register when said light sensor detects a light beam, which in turn may create a time stamp. In turn, the created time stamp may trigger the start of a timer.

According to another aspect, the monitoring device may further comprise a user information interface capable of providing information to a user. The user information interface may comprise a display as well as other types of indicators such as lamps, audio generating elements and vibrating elements.

According to a further aspect, the monitoring unit may comprise a touch sensor, wherein the touch sensor may be operably connected to the electronics circuit such that the electronics circuit is activated when the touch sensor detects a touch or a movement of the monitoring unit. This feature will save power of the monitoring device in that it can be put in inactive or sleep mode when not used, and may be activated when a user picks up a medicament delivery device having a monitoring unit attached.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which

DETAILED DESCRIPTION

Figure 1:
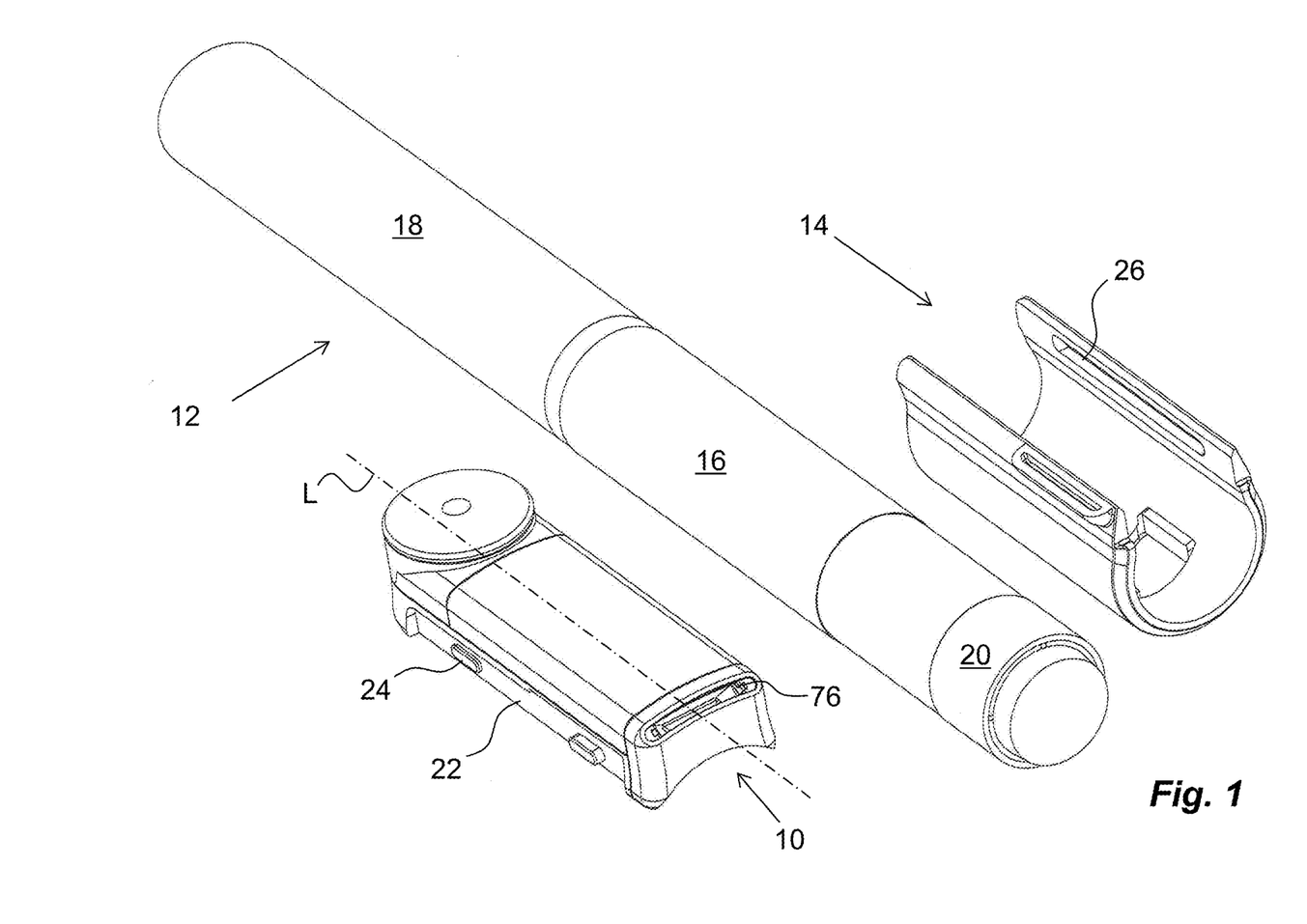
FIG. 1 is a perspective view of a monitoring unit and a fastening element, which are to be connected to a medicament delivery device.

The present disclosure relates to a smart monitoring device or unit 10 for monitoring the use of medicament delivery devices 12 such as insulin pens as seen in FIG. 1 even though it should be understood that a number of different medicaments may be delivered by the medicament delivery device. The monitoring unit 10 may be connected to the medicament delivery device 12 in a number of ways. In one example the monitoring unit may be an integral part of the medicament delivery device with its different components, elements and functions provided inside a housing of the medicament delivery device. In addition, the monitoring unit may be connected to a standard, conventional medicament delivery device by suitable connecting elements. FIG. 1 shows one example of a connecting element in the form of an annular sleeve 14 that is designed to be removably mounted on the outside of the medicament delivery device in a secure way. In this regard, the sleeve 14 is preferably adapted to the outer shape and dimensions of the medicament delivery device it is intended to be connected to.

The type of medicament delivery device that the monitoring unit is intended to be connected to comprises a generally elongated tubular housing body 16. The housing body is arranged to accommodate a medicament container, wherein the medicament container is provided with a medicament delivery member such as an injection needle. The medicament delivery member could either be an integral part of the medicament container or be attachable to the proximal part of the medicament container via suitable attachment elements such as threads, bayonet connections, luer connections etc. At the proximal end of the body a protective cap 18 may be releasibly attached for protecting the medicament delivery member before use.

Further, a dose activation element 20 in the form of a button at the distal end of the medicament delivery device is provided. The dose activation element 20 is turned or moved in order to set a certain prescribed dose, which preferably may be shown with suitable indicia on or adjacent the dose activation element. When a dose is being set, the dose activation element 20 is moved in the distal direction in relation to the housing 16 and when delivering a dose of medicament, the user presses on the distal end of the dose activation element whereby it is moved in the proximal direction back to its initial position. During this movement, the dose activating element 20 is acting on dose delivery elements, such as plunger rods, which in turn act on stoppers inside the medicament container, whereby a dose of medicament is expelled through the medicament delivery member.

The monitoring unit 10 according to the embodiment shown is intended to be connected to a conventional medicament delivery device. The monitoring unit 10 comprises a generally rectangular housing 22, FIGS. 1 and 2. The outer side surfaces of the housing 22 are arranged with attachment elements 24 that are to interact with corresponding attachment elements 26 of the connecting element 14. In the embodiment shown in the drawings, the attachment elements 24 of the monitoring unit 10 comprises outwardly directed protrusions, which are designed to fit into longitudinally extending grooves 26 on oppositely directed inner surfaces of the connecting element 14. It is however to be understood that other types of attachment elements may be utilised in order to provide a positive and firm attachment of the monitoring unit. For example, if the orientation of the monitoring unit in relation to the fastening element and the medicament delivery device is important, a proximal area of the monitoring unit may be arranged with protrusions in one end of the housing and recesses in the other end of the housing and that the fastening element comprises complementary attachment elements so that the monitoring unit may only be attached to the fastening element in one direction. The lower part of the housing 22, which is directed towards a medicament delivery device when fastened, is somewhat curved or concave to follow the curvature of the medicament delivery device. The monitoring unit is further arranged with an end piece 30 that is attachable to an end surface of the housing. A lower surface 32 of the end piece has the same curvature as the lower part of the housing 22, FIG. 2. The lower surface 32 of the end piece 30 is designed with cut-outs 34, which cut-outs form passages 34 when the end piece 30 is attached to the housing as seen in FIG. 3, the function of which will be described below.

Figure 2:
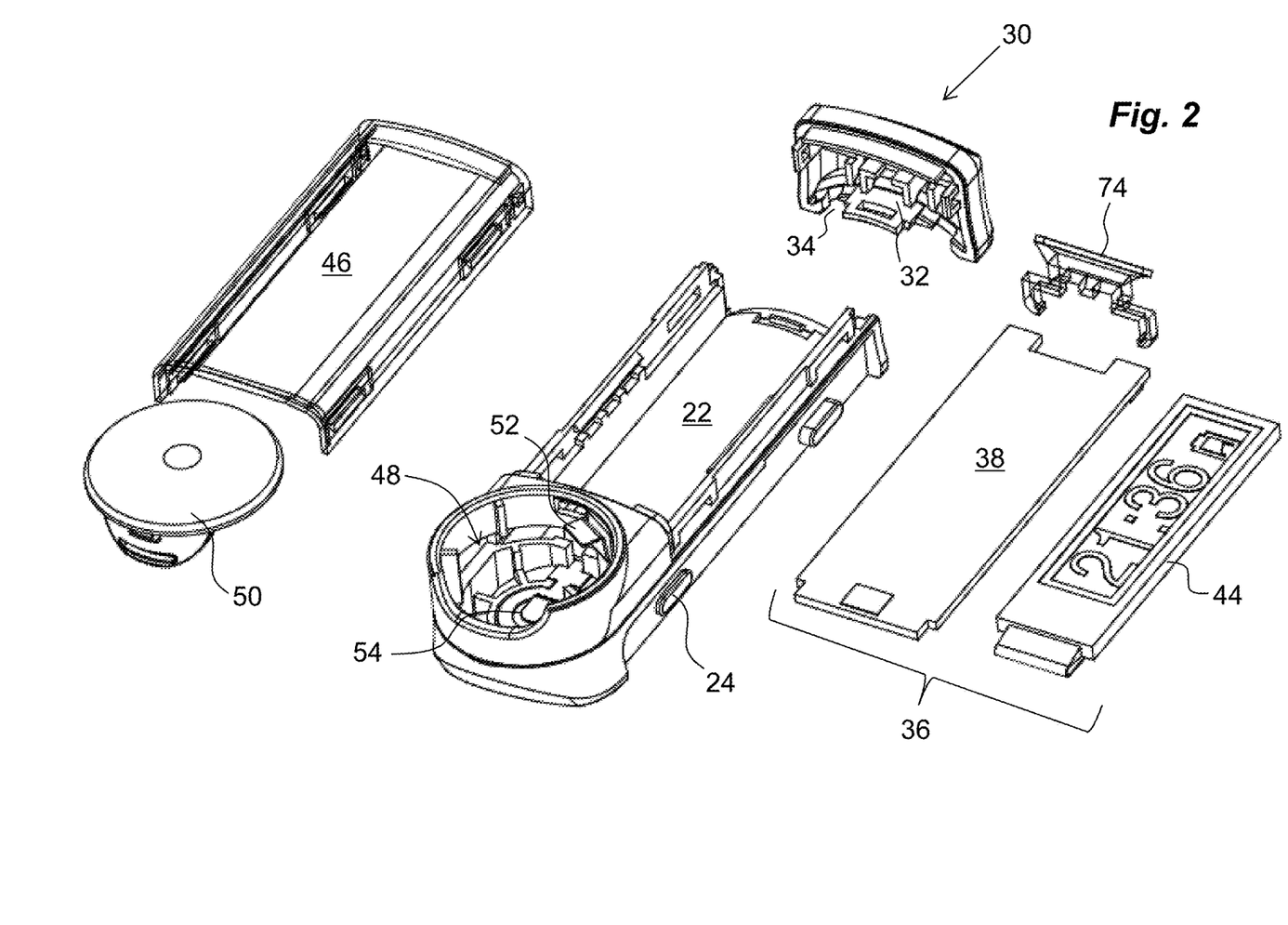
FIG. 2 is an exploded view of the monitoring unit of FIG. 1.
Figure 3:
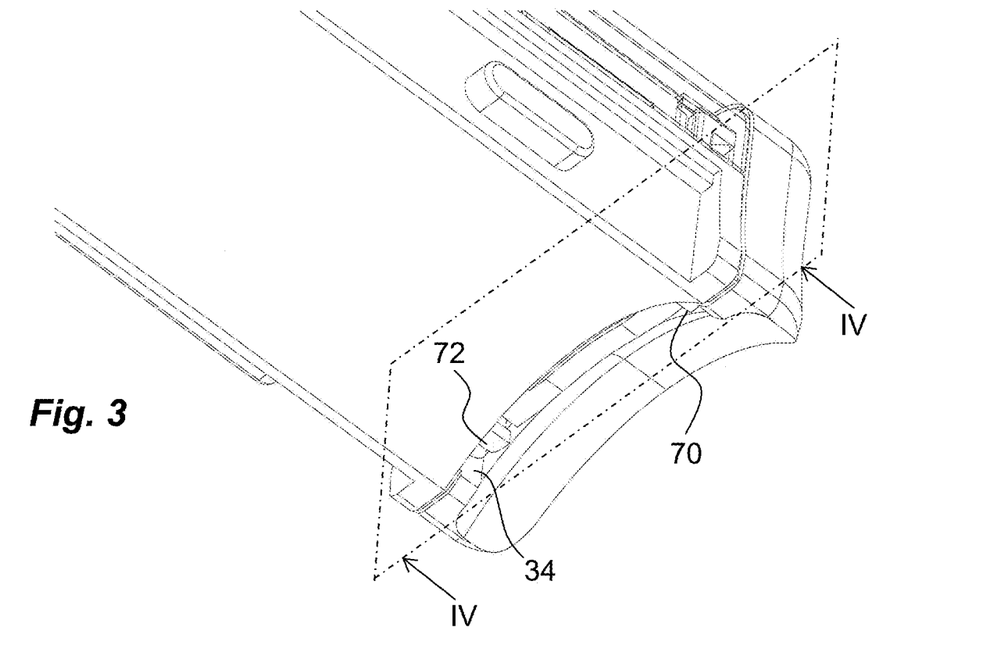
FIG. 3 is a perspective view of a distal part of the monitoring unit of FIG. 1.
Figure 5:
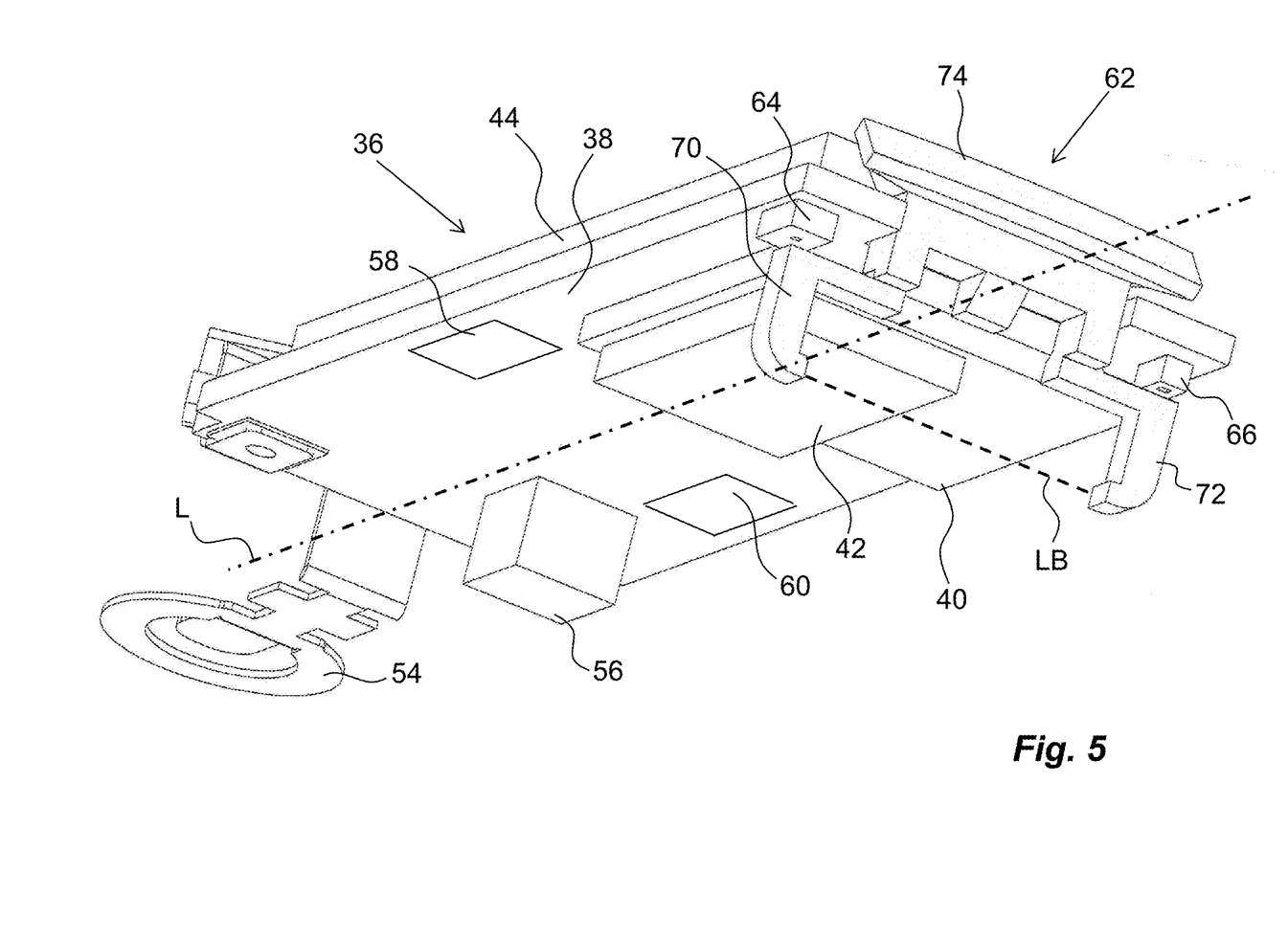
FIG. 5 is a detailed view of an electronics circuit and an activation mechanism comprised in the monitoring unit of FIG. 1, FIG. 6 and FIG. 7 are perspective views of a distal area of a medicament delivery device with an attached monitoring unit.

The monitoring unit 10 is further arranged with an electronic circuit 36, FIGS. 2 and 5. The electronic circuit 36 is preferably arranged on a printed circuit board 38 and is provided with a micro-controller unit 40 or MCU arranged to perform different functions based on program code. The electronic circuit 36 is further arranged with memory storage elements 42 in which the program code may be stored as well as data information obtained during operation of the monitoring unit 10. A user communication element in the form of a display 44, FIG. 2, is operationally connected to the electronic circuit 36, which display 44 is placed on an upper part of the housing 22 and is protected by a transparent cover 46. Apart from, and/or in addition to the display 44, the monitoring unit may be provided with further user communication elements such as LED-elements having e.g. different colours and/or flashing functions, vibrating elements, audio generating elements capable of creating sounds and even voice messages. The electronics circuit 30 is powered by a suitable power source that in the embodiment shown may be a button cell that is placed in an appropriate compartment 48 inside the housing. The button cell is held stationary by a removable lid 50. Suitable connecting leads 52, 54 are arranged between the electronics circuit and the poles of the button cell.

The electronic circuit 36 is preferably arranged with a communication module 56, FIG. 5, that is capable of transmitting and receiving data. Preferably the communication module 56 comprises modules for wireless communication with external devices. Preferably, but not exclusively, the modules for wireless communication use short-range wireless technologies such as for example ANT+, Bluetooth, NFC, RFID, Wi-Fi, Wireless HART, ZigBee, Z-wave, etc. At present, Bluetooth technology is preferred, being widely spread and included in many so called smart devices, but other communication technologies are naturally feasible.

The electronics circuit may further be arranged with different types of sensors operably capable of providing information regarding status of the monitoring unit. The sensors may include touch sensors 58 and temperature sensors 60 for instance. Further, according to the disclosure, the monitoring unit comprises an activation mechanism 62 operably connected to the dose activating element 20. The activation mechanism 62 comprises a light emitting element 64 and a light detecting sensor 66. The light emitting element 64 and the light sensor 66 are positioned such that a light beam from the light emitting element 64 can be received and detected by the light element 66 when the beam is undisrupted.

The activation mechanism 62 is arranged such so as to detect when a dose has been delivered to a patient. As mentioned above, a dose is set when dialing or turning the dose activating element 20, whereby it is moved in the distal direction and a dose is delivered when the dose activating element 20 is moved or pushed back to its initial position. Due to that, the activation mechanism 62 is placed such that the beam from the light emitting element 64 is interrupted in the initial position of the dose activating element, but is uninterrupted in other positions of the dose activating element.

Figure 4:
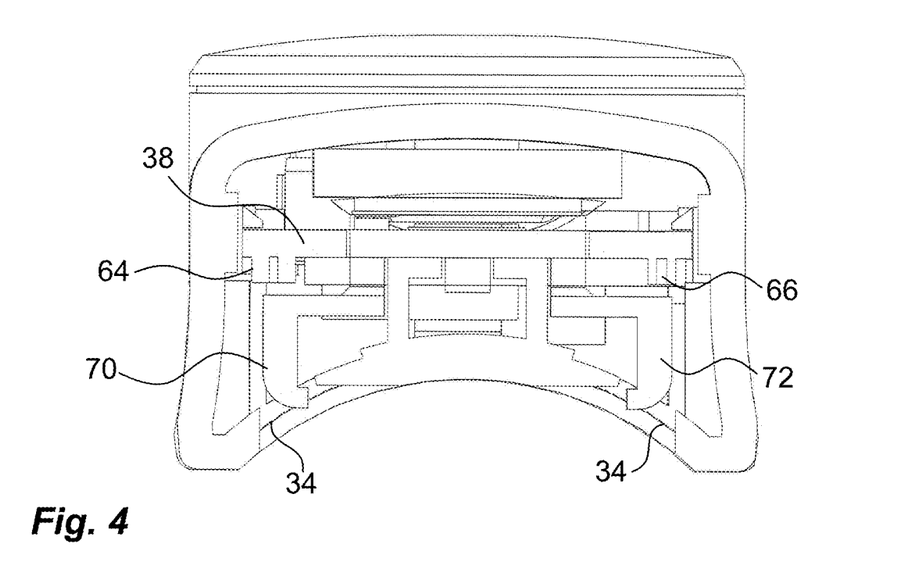
FIG. 4 is a cross-sectional view taken along the plane IV-IV of FIG. 3.

One solution to this is to have a light beam LB that is directed transversal to the longitudinal axis L of the device as seen in FIG. 5. The light beam LB is given that direction by a first light guide 70 placed with an entrance surface in the vicinity of the light emitting element 64. The first light guide is curved 90 degrees with an exit surface directed transversal to the longitudinal axis. The exit surface is positioned in one of the passages 34 of the housing as seen in FIG. 4. A second light guide 72 is placed with an entrance surface positioned in the other passage 34 and aligned with and facing the exit surface of the first light guide 70, FIGS. 4 and 5. The second light guide 72 is also curved 90 degrees and is provided with an exit surface adjacent the light sensor 66 as seen in FIGS. 4 and 5. Thus, if a light beam is emitted from the light emitting element 64 it will enter the first light guide 70 and be diverted 90 degrees towards the second light guide 72, enter the second light guide 72 and be diverted again 90 degrees and hit the light sensor 66. Further, the light guides may be an integral part of a component 74 that is attached to the end piece 30 and be of a generally light spreading material. Thus, a part of the component 74 may be placed in an opening 76 of the end piece 30, FIG. 1, and when the light emitting element 64 is active, the component 74 is lit up, visibly, in the opening 76 of the end piece 30, informing a user that the monitoring unit is active and is monitoring the use of the medicament delivery device.

Figure 6:
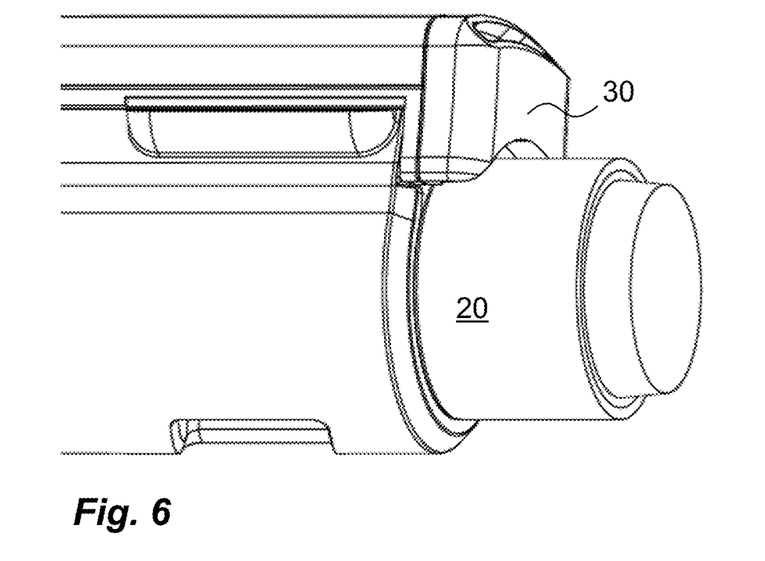

The activation mechanism 62 is placed in the housing of the monitoring unit such that when the fastening element 14 is properly attached to the medicament delivery device with the dose activating element 20 in the initial position and with the monitoring unit 10 connected to the fastening element 14, the exit surface of the first light guide 70 is placed on one side of the dose activating element 20 and the entrance surface of the second light guide 72 is placed transversally on the other side of the dose activating element 20, FIG. 6.

When the medicament delivery device is to be used the connecting element 14 is attached to the housing in the proper position. In this regard, the connecting element 14 and/or the medicament delivery device 12 may be arranged with ledges, steps, grooves, protrusions or with similar mechanical reference points that ensure a proper position. A monitoring unit 10 is then connected to the fastening element 14 and is powered up, which may be done by connecting the power source to the electronic circuit. If left for a set amount of time without touching the medicament delivery device, the MCU 40 is designed to set the monitoring unit in a low power mode so as to save energy.

If the medicament delivery device is picked up by a user in the low power mode, the touch sensor 58 detects that the medicament delivery device has been touched, which will cause the monitoring unit 10 to be activated. The activation of the monitoring unit 10 will cause the MCU 40 to activate the light emitting element 64 such that a light beam LB enters the first light guide 70, which light beam LB is diverted 90 degrees and exits the first light guide 70. However, because the dose activating element 20 is in its initial position, the light beam exiting the first light guide 70 will be interrupted by the dose activating element 20 and will thus not reach the light sensor 66. The activation of the monitoring unit 10 will also cause the MCU 40 to activate the display 44 and send data to the display such that different information is visible. There could be many types of information that are displayed such as time of day, battery status, elapsed time since last dose and even error messages. Regarding elapsed time since last dose, the MCU 40 has the ability to keep track of time and to create and store time stamps at certain occurrences as will be described.

Figure 7:
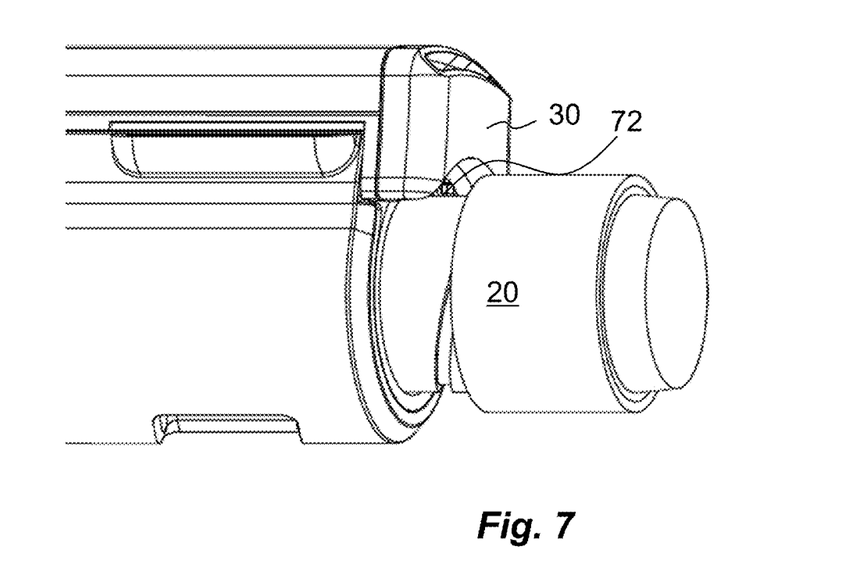

When now a dose is to be set and delivered, the user turns or dials the dose activating element 20 whereby it is moved in the distal direction. This in turn causes the blocking of the light beam to cease whereby the light beam can hit the second light guide 72, be diverted 90 degrees and cause it to hit the light sensor 66, FIG. 7. This will in turn cause the MCU 40 to register the signal from the light sensor 66. The registration will cause the MCU 40 to create a time stamp that is stored in the memory elements. Further, the MCU 40 may now change the information on the display to the current time and to remove the elapsed time.

The user continues to operate the dose activating element until the proper and prescribed dose is set. The medicament delivery member is then placed at the dose delivery site and with an injection needle a penetration is performed. The user again acts on the dose activating element 20 by moving or pushing it in the proximal direction, whereby a dose delivery sequence is performed. When the dose activating element 20 has returned to its initial position, the dose delivery sequence has ended and the medicament delivery device can be removed from the dose delivery site.

As mentioned above, when the dose activating element 20 is back in its initial position, the light beam will again be interrupted by the dose activating element, which in turn causes a deactivation of the light sensor 66. This deactivation of the light sensor 66 will be registered by the MCU 40 which will cause the MCU 40 to create another time stamp and also to count up the time and display it. Further, the MCU 40 activates the communication module 56 to "listen"

to any requests from external devices such as Bluetooth requests from smart devices, preferably at certain intervals and not continuously, for saving power. If contacted by e.g. a Bluetooth request from an external device and the particular external device has previously been validated by a pairing operation with the monitoring unit, the monitoring unit may transmit data to the smart device. The data could for example be the time stamps registered and stored by the MCU 40. Further data could for example be temperature readings if the electronics circuit is provided with a temperature sensor. In this regard, in order to save energy, the monitoring unit is activated from low power mode at certain intervals to collect data and then returns to the low power mode.

Figure 8:
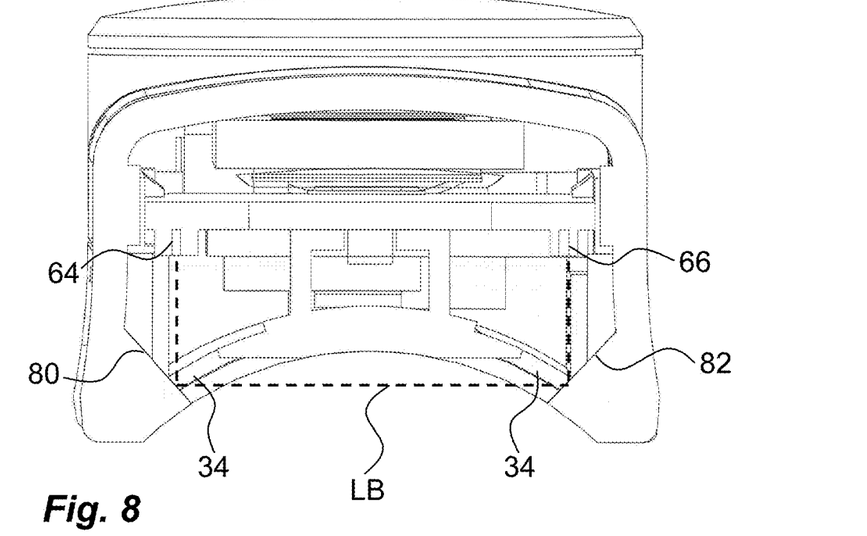
FIG. 8 and FIG. 9 are cross-sectional views taken along the plane IV-IV of FIG. 3 of alternative embodiments to the activation mechanism.
Figure 9:
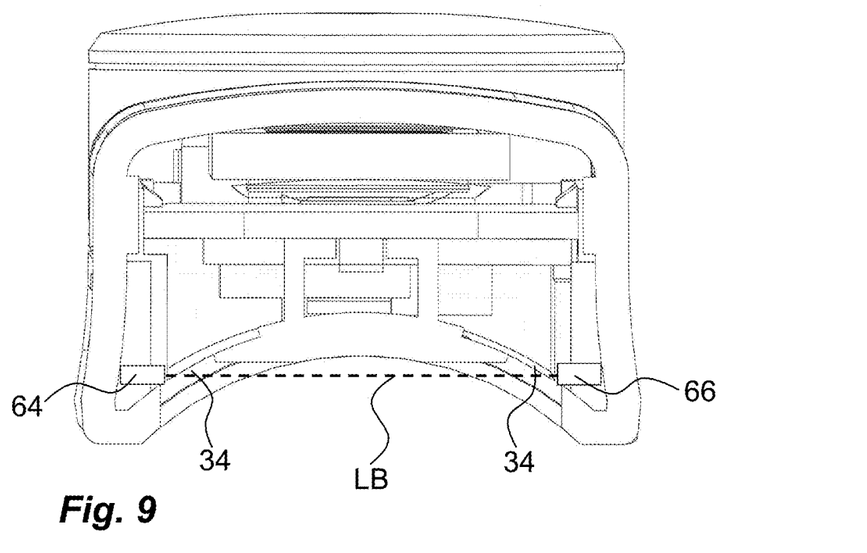

There are of course a number of modifications that are feasible within the present disclosure. One possible solution is to make the light guides as flat reflecting surfaces 80, 82 that are angled such that a 90 degree deflection is obtained, see FIG. 8. Another feasible solution is to place the light emitting element 64 and the light sensor 66 directly opposite each other without any light guides, as seen in FIG. 9.

It is to be understood that the embodiments described above and shown in the drawings are to be regarded only as non-limiting examples of the disclosure and that it may be modified in many ways within the scope of the patent claims.

The invention claimed is:

1. A monitoring device arranged to be operably connected to a medicament delivery device, said monitoring device comprising:
   an electronic circuit comprising a light emitting element and a light sensor;
   a first light guide positioned with an entrance surface adjacent the light emitting element, wherein the first light guide is curved such that an exit surface of the first light guide is positioned in a different plane than the entrance surface; and
   a second light guide positioned with an exit surface adjacent the light sensor, wherein the second light guide is curved with an entrance surface facing the exit surface of the first light guide,
   wherein said light emitting element and said light sensor are configured to be positioned in relation to a dose activating element of the medicament delivery device so as to detect a manual operation of said dose activating element from an initial position, and
   wherein said electronics circuit is arranged to register when said light sensor detects an interruption of a light beam between said light emitting element and said light sensor.

2. The monitoring device according to claim 1, wherein said dose activating element is arranged for setting a dose of medicament and for delivering said set dose.

3. The monitoring device according to claim 2, wherein said light emitting element and said light sensor are positioned in relation to said dose activation element so that the light beam between said light emitting element and said light sensor is interrupted when said dose activation element is in its initial position, is uninterrupted when said dose activating element is moved from its initial position, and is again interrupted when said dose activating element is returned to its initial position after delivery of a dose.

4. The monitoring device according to claim 1, wherein said electronic circuit is arranged to register when said light sensor detects the light beam.

5. The monitoring device according to claim 4, wherein the registering creates a time stamp.

6. The monitoring device according to claim 1, wherein the registering creates a time stamp.

7. The monitoring device according to claim 6, wherein the time stamp triggers a start of a timer.

8. The monitoring device according to claim 1, further comprising a user information interface capable of providing information to a user.

9. The monitoring device according to claim 8, wherein the user information interface comprises a display.

10. The monitoring device according to claim 1, further comprising a touch sensor.

11. The monitoring device according to claim 10, wherein the touch sensor is operably connected to the electronics circuit such that the electronics circuit is activated when the touch sensor detects a touch or a movement of the monitoring device by a user.

12. The monitoring device according to claim 1, further comprising a temperature sensor.

13. The monitoring device according to claim 1, wherein the first light guide is curved 90 degrees with the exit surface directed transverse to a longitudinal axis of the monitoring device, and wherein the second light guide is curved 90 degrees.

14. A monitoring device configured for operable connection to a medicament delivery device, the monitoring device comprising:
   an electronic circuit comprising a light emitting element and a light sensor, wherein the light emitting element and the light sensor are configured to be positioned in relation to a dose activating element of the medicament delivery device so as to detect axial distal movement of the dose activating element from an initial position, and wherein said electronics circuit is arranged to register when said light sensor detects an interruption of a light beam between said light emitting element and said light sensor;
   a first light guide positioned with an entrance surface adjacent the light emitting element, wherein the first light guide is curved such that an exit surface of the first light guide is positioned in a different plane than the entrance surface;
   a second light guide positioned with an exit surface adjacent the light sensor, wherein the second light guide is curved with an entrance surface facing the exit surface of the first light guide; and
   a touch sensor operably connected to the electronics circuit such that the electronics circuit is activated when the touch sensor detects a touch or a movement of the monitoring device by a user.

15. The monitoring device according to claim 14, wherein the light emitting element and the light sensor are positioned in relation to the dose activation element so that the light beam between the light emitting element and the light sensor is interrupted when the dose activation element is in the initial position and is uninterrupted when the dose activating element is moved from its initial position to set a dose.

* * * * *